United States Patent
Subramanian et al.

(10) Patent No.: US 8,712,499 B2
(45) Date of Patent: Apr. 29, 2014

(54) QUANTITATIVE OXYGEN IMAGING SYSTEMS AND METHODS USING ECHO-BASED SINGLE POINT IMAGING

(75) Inventors: Sankaran Subramanian, Rockville, MD (US); Nallathamby Devasahayam, Germantown, MD (US); Shingo Matsumoto, Rockville, MD (US); James B. Mitchell, Damascus, MD (US); Murali Krishna Cherukuri, North Potomac, MD (US); John A. Cook, Bethesda, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 160 days.

(21) Appl. No.: 13/131,165

(22) PCT Filed: Nov. 25, 2009

(86) PCT No.: PCT/US2009/065956
§ 371 (c)(1),
(2), (4) Date: Aug. 17, 2011

(87) PCT Pub. No.: WO2010/062973
PCT Pub. Date: Jun. 3, 2010

(65) Prior Publication Data
US 2011/0313279 A1    Dec. 22, 2011

Related U.S. Application Data

(60) Provisional application No. 61/200,579, filed on Nov. 29, 2008.

(51) Int. Cl.
A61B 5/055    (2006.01)

(52) U.S. Cl.
USPC .......................................... 600/410; 600/407

(58) Field of Classification Search
USPC .......................... 600/407, 410; 324/318–322
See application file for complete search history.

(56) References Cited

U.S. PATENT DOCUMENTS

| | | | |
|---|---|---|---|
| 4,896,113 A | 1/1990 | Pelc | |
| 5,632,276 A * | 5/1997 | Eidelberg et al. | 600/414 |
| 6,279,377 B1 | 8/2001 | Cao | |
| 2008/0057590 A1 | 3/2008 | Urdea et al. | |

OTHER PUBLICATIONS

Fang et al. Combination of Magic-Echo and Single-Point Imaging Techniques for Solid-State MRI. Appl. Magn. Reson. 2002; 22: 269-276.*
Subramanian et al. Dancing with the Electrons: Time-Domain and CW in vivo EPR Imaging. Magn Reson Insights. 2008; 2: 43-74.*

(Continued)

*Primary Examiner* — Peter Luong
(74) *Attorney, Agent, or Firm* — Polsinelli PC; Teddy C. Scott, Jr.; Ron Galant (57) ABSTRACT

An echo-based single point imaging (ESPI) system (10) providing high-resolution oxygen images of a sample is disclosed. The ESPI system (10) employs spin echo detection of the resonance from a spin probe and concurrent Single Point Imaging (SPI) for spatial encoding of the oxygen concentration within the sample. Images are derived by comparing spin echo intensities of two images reconstructed at two time points selected at identical time intervals on either side of a refocusing pulse, eliminating artifacts associated with sample magnetic susceptibility and field inhomogeneity effects.

16 Claims, 9 Drawing Sheets

(56) References Cited

OTHER PUBLICATIONS

Subramanian et al. Single-Point (Constant-Time) Imaging in Radiofrequency Fourier Transform Electron Paramagnetic Resonance. Magnetic Resonance in Medicine. 2002; 48: 370-379.*

Beyea, S.D. et al., Imaging of Heterogeneous Materials with a Turbo Spin Echo Single-Point Imaging Technique, Journal of Magnetic Resonance, Academic Press, Orlando, FL, US, vol. 144, No. 2, 2000, pp. 255-265.

Zhang, Z., et al., Spatial and temporal mapping of water content across Nafion membranes under wetting and drying conditions, Journal of Magnetic Resonance, Academic Press, Orlando, FL, US, vol. 194, No. 2, Oct. 1, 2008, pp. 245-253.

Beyea, S.D., et al., Relaxation Time Mapping of Short ShortT<*>2Nuclei with Single-Point Imaging (SPI) Methods, Journal of Magnetic Resonance, Academic Press, Orlando, FL, US, vol. 135, No. 1, Nov. 1, 1998, pp. 156-164.

Matsumoto, Ken-Ichiro, et al., Electron paramagnetic resonance imaging of tumor hypoxia: Enhanced spatial and temporal resolution for in vivo pO2 determination, Magnetic Resonance in Medicine, vol. 55, No. 5, Apr. 4, 2006, pp. 1157-1163.

Choi, S. et al., Contant Time Imaging Approaches to NMR Microscopy, International Journal of Imaging Systems and Technology, Wiley and Sons, New York, US, vol. 8, No. 3, 1997, pp. 263-276.

Ouriadov, A.V. et al., Thin film MRI-high resolution depth imaging with a local surface coil and spin echo SPI, Journal of Magnetic Resonance, Academic Press, Orlando, FL, US, vol. 169, No. 1, 2004, pp. 174-186.

MA, J., et al., Method for image-based measurement of the reversible and irreversible contribution to the transverse-relaxation rate, Journal of Magnetic Resonance, Series B, Academic Press, Orlando, FL, US, vol. 111, No. 1, Apr. 1, 1996, pp. 61-69.

* cited by examiner

QUANTITATIVE OXYGEN IMAGING SYSTEMS AND METHODS USING ECHO-BASED SINGLE POINT IMAGING

CROSS-REFERENCE TO RELATED APPLICATIONS

This is the national stage of International Application No. PCT/US2009/065956, filed on Nov. 25, 2009, which claims the benefit of U.S. Provisional Patent Application No. 61/200,579, filed on Nov. 29, 2008, the contents of all of which are incorporated herein by reference.

FIELD

This document relates to tissue imaging and in particular to a system for in vivo issue oxygen imaging via pulsed time-domain electron paramagnetic resonance using cooperative electron spin echo and single point imaging.

BACKGROUND

Electron Paramagnetic Resonance (EPR) is a spectroscopic technique that is analogous to Nuclear Magnetic Resonance (NMR). EPR spectroscopy detects species with unpaired electrons such as transition metal ions and free radicals, rather than the magnetic nuclei such as $^1H$, $^{13}C$, and $^{19}F$ detected using NMR spectroscopy methods. Magnetic Resonance Imaging (MRI) employs magnetic field gradients to generate anatomic images from objects that have a significant amount of water protons therein. The contrast agent-induced spectral changes such as changes in spin-lattice relaxation ($T_1$) and spin-spin relaxation ($T_2$) times of protons provide functional information. Recently available biologically compatible free radical contrast agents have made in vivo EPR imaging feasible using methods similar to MRI methods. However, the spectral changes in EPR are much more sensitive to local environment than in MRI, making EPR imaging a potentially useful functional imaging technique.

EPR techniques may be executed in a continuous wave (CW) mode using a relatively slow field-swept mode, or by using pulses as in MRI in a constant magnetic field, which may obtain data much more quickly. However, pulsed EPR methods utilize paramagnetic spin probes having very narrow line widths to achieve sufficient capture of the impulse response of magnetization in the presence of magnetic field gradients for image formation. Numerous narrow line width spin probes based on triarylmethyl (trityl) radical are available that may be used for time-domain EPR imaging.

Spin echo Fourier transform imaging is a procedure in which a subject may be perfused with a narrow-line paramagnetic spin probe and then subjected to a 90°-t-180° or a general θ-t-2θ pulse pair. At a specified time from the first 90° pulse that depends on the timing of the second 180° pulse, an echo is received in which the echo peak height is attenuated by spin-spin relaxation. Fourier transform of the echo measured within a series of frequency encoding linear magnetic field gradients generates a spatial projection of the echo. A series of spatial projections generated as a function of the gradient vector orientation at equal angular intervals in a plane generated projections that may be subjected to filtered back projection to give a two-dimensional image of the object projected on to the plane of the gradient rotation. The plane of rotation of the linear magnetic field gradients may also be rotated in order to sweep a spherical volume centered on the object, and a two-step filtered back projection may be used to generate a three-dimensional image. The quality and resolution of the image depends on at least several factors including but not limited to the line width of the spin probe, the magnitude of the gradient, and the spacing of the gradient rotation angles.

The second pulse refocuses any line broadening brought about by the gradient-induced $T_2^*$ and the intrinsic magnetic susceptibility of the subject. Images formed by the filtered back projection from echoes are weighted in contrast by the relaxation time $T_2$, which depends linearly on the oxygen content at each spatial location within the subject. Quantitative oxymetric information may be derived from a series of $T_2$-weighted images as a function of the echo time. Conventional 90°-180° spin echo pulse sequence images may be obtained by the filtered back-projection of the frequency-encoded projections obtained by the Fourier transform of spin echoes. The spin echo Fourier transform method yields oxymetric data that is well-suited for clinical applications, however the spatial resolution of the imaging is not of sufficient quality for EPR imaging.

Multi-gradient Single Point Imaging (SPI) is another approach to tissue imaging that utilizes pure phase encoding in which the oxymetric data are $T_2^*$-based. This approach relies on apparent line width evaluations that may be vulnerable to degradation due to factors including but not limited to the intrinsic magnetic susceptibility of the subject and non-homogeneity of the magnetic field that may be ameliorated using system-specific calibrations using reference standards. While SPI imaging gives superior spatial resolution, oxygen quantization in this procedure may need careful calibration to yield sufficiently accurate oxymetric results.

A need in the art exists for a tissue imaging method that combines the excellent spatial resolution of SPI imaging and the highly accurate oxymetric information obtainable using spin echo Fourier transform imaging procedures.

SUMMARY

In one embodiment, a method of producing a high-resolution quantitative oxygen image of a sample may include determining at a echo-based single point imaging (ESPI) oxygen imaging system executed on at least one processor a spatially-resolved relaxivity between each of a plurality of first logarithms of spatially-resolved spin intensities of a first ESPI image and each of a plurality of corresponding second logarithms of spatially-resolved spin intensities of a second ESPI image. The ESPI oxygen imaging system may then determine a spatially-resolved oxygen content by interpolating a reference oxygen concentration from a predetermined table including a plurality of reference oxygen concentrations as a function of the spatially-resolved relaxivity, and maps each spatially-resolved oxygen content onto a corresponding spatial location within a sample image to produce a high-resolution quantitative oxygen image.

In another embodiment, a method of producing a high-resolution quantitative oxygen image of a sample may include providing at least two high-resolution ESPI images of the sample including a first ESPI image having a reconstruction of a plurality of first EPR signals measured at a time Δt prior to a focusing pulse, and further including a plurality of spatially-resolved logarithms of first spin intensities, wherein each of the first spin intensities is mapped to one of a plurality of spatial positions within a sample image. A second ESPI image may include a reconstruction of a plurality of second EPR signals measured at a time Δt after the focusing pulse, and further including a plurality of spatially-resolved logarithms of second spin intensities, wherein each second spin intensity is mapped to one of the plurality of spatial positions within the sample image. The method further includes determining for each one of the plurality of spatial positions within the sample image a spatially-resolved relaxivity between each of the plurality of first logarithms of spatially-resolved spin intensities of the first ESPI image and each of the plurality of corresponding second logarithms of spatially-resolved spin intensities of the second ESPI image. The method then determines for each one of the plurality of spatial positions within the sample a spatially-resolved oxygen content by interpolating a reference oxygen concentration from a predetermined table including a plurality of reference oxygen concentrations as a function of spatially-resolved relaxivities, and maps each spatially-resolved oxygen content onto a corresponding spatial location within a sample image to produce the high-resolution quantitative oxygen image.

In yet another embodiment, a system for producing a high-resolution quantitative oxygen image of a sample may include a plurality of modules to be executed on at least one processor. The plurality of modules may include an ESPI image comparison module to derive a spatially-resolved relaxivity between each of a plurality of first logarithms of spatially-resolved spin intensities of a first ESPI image and each of a plurality of corresponding second logarithms of spatially-resolved spin intensities of a second ESPI image. An oxygen imaging module may determine a spatially-resolved oxygen concentration by interpolating a reference oxygen concentration from a predetermined table comprising a plurality of reference oxygen concentrations as a function of the spatially-resolved relaxivity, and then mapping each spatially-resolved oxygen concentration onto a corresponding spatial location within a sample image to produce the high-resolution quantitative oxygen image.

In one embodiment, a computer-readable media encoded with a ESPI oxygen imaging system for producing a high-resolution quantitative oxygen image. The ESPI oxygen imaging system may include computer-readable instructions executable by at least one processor for performing the steps of deriving a spatially-resolved relaxivity between each of a plurality of first logarithms of spatially-resolved spin intensities of a first ESPI image and each of a plurality of corresponding second logarithms of spatially-resolved spin intensities of a second ESPI image. The ESPI oxygen imaging system then determines a spatially-resolved oxygen concentration by interpolating a reference oxygen concentration from a predetermined table including a plurality of reference oxygen concentrations as a function of the spatially-resolved relaxivity, and then mapping each spatially-resolved oxygen concentration onto a corresponding spatial locations within the sample to produce the high-resolution quantitative oxygen image.

Additional objectives, advantages and novel features will be set forth in the description which follows or will become apparent to those skilled in the art upon examination of the drawings and detailed description which follows.

BRIEF DESCRIPTION OF THE DRAWINGS

The following figures illustrate various aspects of the embodiments described herein.

Corresponding reference characters indicate corresponding elements among the view of the drawings. The headings used in the figures should not be interpreted to limit the scope of the claims.

DETAILED DESCRIPTION

Various embodiments of the invention provide systems and methods of producing high-resolution in vivo quantitative tissue oxygen imaging. As will be described in detail below, the in vivo $pO_2$ images produced using the Echo-based Single Point Imaging (ESPI) system provide superior resolution compared to previous methods. In particular, resolution in the ESPI system is unaffected by line width of the spin probe. Various embodiments of the ESPI system provide estimates of $pO_2$ of a sample based on accurate measurements of $T_2$ that are unaffected by system-specific factors including but not limited to magnetic susceptibility of the sample, magnetic field inhomogeneity and most other time-dependent Hamiltonians, which are essentially eliminated by the use of spin-echo imaging techniques by the ESPI system.

Non-limiting examples of samples that may be analyzed using the ESPI system may be chemical compounds, tissue homogenates, cultured cells, and whole living organisms including but not limited to invertebrate animals, fish, amphibians, reptiles, birds, and mammals. In an embodiment, the maximum size of living organisms that may be analyzed using the ESPI system is limited only by the size of the chamber of the EPR scanner used to produce the EPR data used by the ESPI system to produce the in vivo $pO_2$ images.

Echo-Based Single Point Imaging (ESPI) System

Referring to the drawings, a non-limiting exemplary embodiment of an ESPI system is illustrated and generally indicated as 10 in FIGS. 1-6. The ESPI system 10 may be used to obtain a high-resolution in vivo quantitative tissue oxygen imaging using a combination of electron spin-echo imaging and single point imaging techniques.

Figure 1:
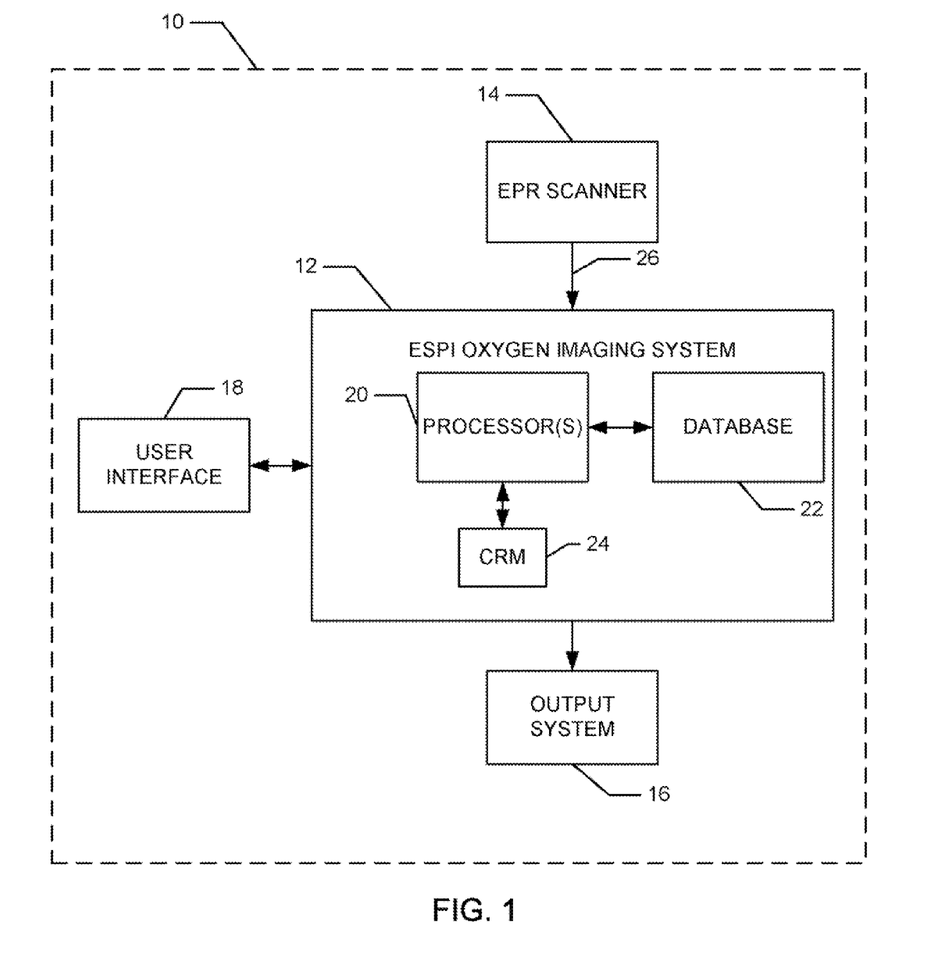
FIG. 1 is a block diagram illustrating a non-limiting exemplary embodiment of an echo-based single point imaging (ESPI) system.

Referring to FIG. 1, a non-limiting exemplary embodiment of a echo-based single point imaging (ESPI) system 10 may produce two or more high-resolution images of a sample using a single point imaging technique at selected time points and further process the high-resolution images using a modification of electron-spin imaging techniques to obtain a high-resolution mapping of the oxygen content of the sample. The ESPI system 10 may include a ESPI oxygen imaging system 12 which may obtain one or more sets of electron paramagnetic resonance (EPR) signals produced by an EPR scanner 14. In one embodiment, each set of EPR signals may include a plurality of time histories of EPR signals measured by the EPR scanner 14. In this embodiment, each time history of EPR signals may be generated using a spin-echo imaging procedure known in the art. In one non-limiting exemplary embodiment. In one non-limiting exemplary embodiment, each time history of EPR signals may be emitted by a sample situated within a magnetic field gradient at a specified spatial orientation in response to irradiation by an excitatory electromagnetic pulse and a focusing electromagnetic pulse. Each time history of EPR signals may include, but is not limited to, a signal peak induced by the excitatory pulse and an attenuated echo pulse induced by the focusing pulse. Using known methods of single-point imaging (SPI), the ESPI oxygen imaging system 12 may assemble a series of at least two images of the sample from the one or more sets of EPR signals, in which each image may correspond to the EPR signals at a specified time. Further, the ESPI oxygen imaging system 12 may determine the oxygen content of the sample by determining the differences in intensity between the two or more images and converting the rate of change in image intensity with respect to time into an oxygen concentration $pO_2$. The oxygen concentration determined by the ESPI oxygen imaging system 12 may be mapped into one or more of the images of the sample to produce a high-resolution oxygen image.

Referring again to FIG. 1, a non-limiting exemplary embodiment of the ESPI oxygen imaging system 12 may use one or more sets of EPR signals produced by an EPR scanner 14 that are communicated to the ESPI oxygen imaging system 12, or alternatively stored in the ESPI oxygen imaging system 12. The EPR scanner 14 may also include one or more devices or systems used to generate or transfer an electronic version of one or more sets of EPR signals to the ESPI oxygen imaging system 12. Once the one or more sets of EPR signals are processed by the ESPI oxygen imaging system 12, the resulting high-resolution mapping of the oxygen content of the sample may be passed to an output system 16 for storage or later analysis. Alternately, the high-resolution mapping of the oxygen content of the sample may be stored at the ESPI oxygen imaging system 12. The ESPI oxygen imaging system 12 may also generate information to the user interface 18, including but not limited to the status of the oxygen imaging process, results, or queries for system input.

In one non-limiting embodiment, the ESPI oxygen imaging system 12 may further include one or more processors 20 that may be embodied by or in one or more distributed or integrated components or systems. The ESPI oxygen imaging system 12 may include a database 22 on which data may be stored and a computer readable media (CRM) 24 on which one or more algorithms, software, modules, data, computer readable instructions, and/or firmware may be loaded and/or operated and/or which may operate on the one or more processors 20 to implement the systems and methods identified herein. In an embodiment, the database 22 may be a storage system that temporarily and/or permanently stores data and may include volatile and/or nonvolatile memory and/or other types of storage systems or devices.

EPR Scanner

As noted above, the ESPI system 10 may include an EPR scanner 14 to generate the EPR time history data from a sample that is subsequently processed by the ESPI oxygen imaging system 12. The EPR scanner 14 may include one or more permanent magnets or electromagnets that may apply a magnetic field to a sample in order to orient the electron spins of the unpaired electrons in the sample. In addition, the EPR scanner 14 may include one or more resonators that may generate one or more electromagnetic pulses that are used to excite the electron spins in the sample. The EPR scanner 14 may further include one or more coils to detect the fluctuations in the magnetic field induced by the excitation of the electron spins in the sample.

Any suitable EPR scanner 14 may be included in the ESPI system 10 including but not limited to commercially available EPR spectrometers. Non-limiting exemplary EPR scanners 14 include a 9.5 GHz EPR spectrometer (Bruker EleXsys E500 with a TE102 resonator, Bruker BioSpin Corp., Billerica, Mass., USA) and a 1 GHz EPR spectrometer (Bruker EleXsys E540 equipped with an L-band bridge, Bruker Bio-Spin Corp., Billerica, Mass., USA). Non-limiting examples of resonators suitable for the ESPI system 10 include imaging resonators, birdcage resonators, and external loop resonators. In an embodiment the resonator may be tuned to a frequency in the range of 100 MHz-2 GHz for in vivo measurements and higher frequency for other imaging purposes.

In one embodiment, a single electromagnetic excitatory pulse may be used to obtain the EPR data that is processed by the ESPI system 10 to produce the one or more high-resolution images of the sample using a SPI technique. In this embodiment, spatial encoding is performed in the presence of magnetic gradients applied in discrete steps along the Cartesian axes, resulting in phase encoding of all the points in the response of the sample as a function of gradient steps and magnitude, as well as the delay of the time point relative to the electromagnetic excitatory pulse. As a result, the effects of line broadening or magnetic field inhomogeneity on image resolution may be minimized.

The pure phase encoding of each time point of the EPR time history data may generate very highly resolved two-dimensional and three-dimensional images by direct Fourier reconstruction. Without being bound to any particular theory, the image resolution depends on user-specified factors including the magnitude and spacing of the different orientations of the magnetic gradients, the number of phase-encoding steps and the location of the time point selected for image reconstruction, but not on the line width of the spin-probe. The reconstructed images may also exhibit a zoom-in effect as a function of the delay of the time point relative to the excitatory signal, and may also exhibit image contrast as a function of $T_2^*$ relaxation phenomena, which may include intrinsic relaxation as modified by the oxygen-content.

Figure 7:
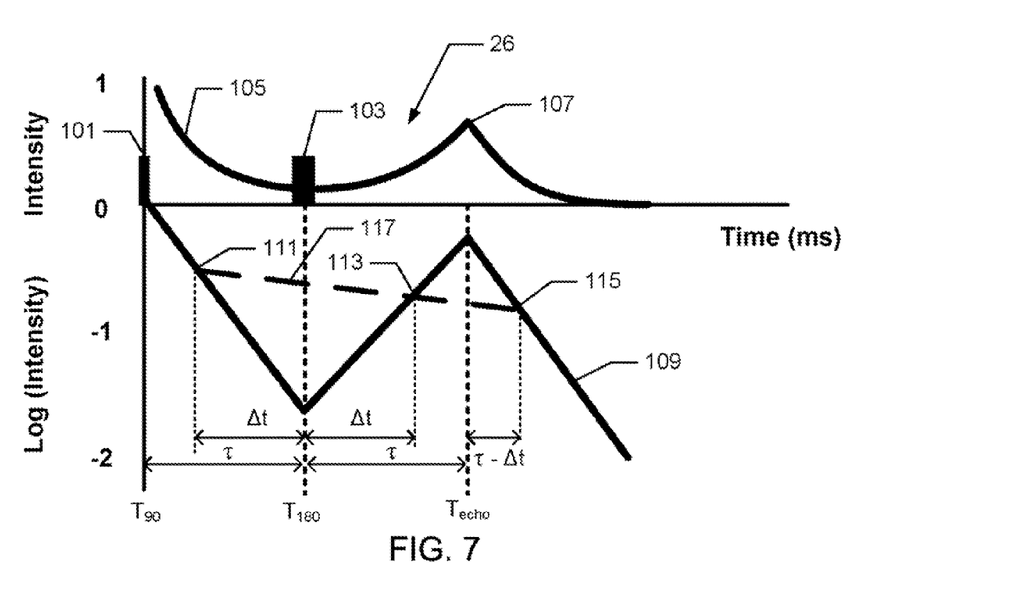
FIG. 7 is a simplified plot of data pursuant to one embodiment of the described echo-based ESPI imaging technique.

FIG. 7 is a graph depicting a non-limiting example of an EPR time history that may be processed by the ESPI system 10. A 90° excitatory pulse 101 applied to the sample at a time $T_{90}$ produces an initial signal peak followed by a free induction decay 105 of the signal governed by $T_1$, $T_2$, and $T_2^*$ relaxation mechanisms. A second 180° focusing pulse 103 applied at a time $T_{180}$ produces an echo peak 107 at a time $T_{echo}$. In this example, the time $T_{180}$ corresponds to a delay time τ after the excitatory pulse time $T_{90}$ and the time $T_{echo}$ at which the echo peak occurs corresponds to a time delay 2τ after the excitatory pulse time $T_{90}$.

The EPR time history illustrated in FIG. 7 illustrates the symmetry of the EPR signals preceding and following the 180° focusing pulse 103. In addition to the symmetry in the magnitude of the EPR signal 26 shown in FIG. 7, the degree of decoherence of the electron spins for pairs of time points located Δt before or after $T_{180}$ is also similar, resulting in similar fields of view when used for image reconstruction.

ESPI Oxygen Imaging System

Figure 2:
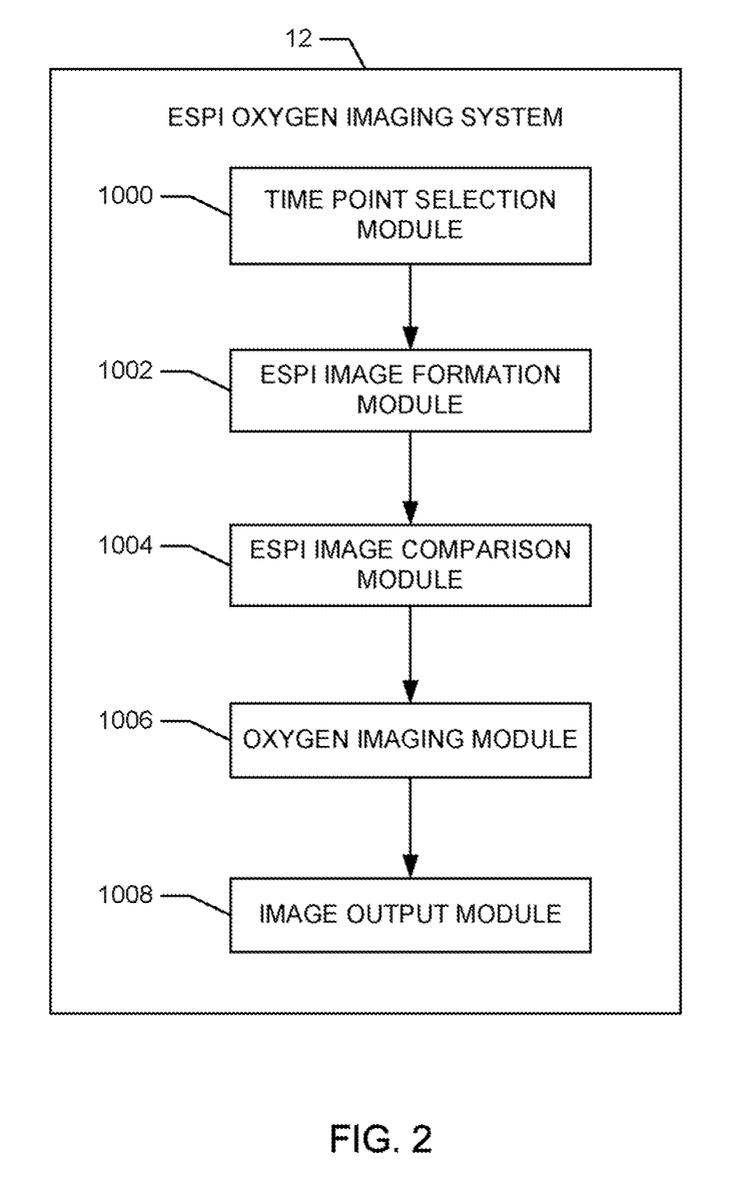
FIG. 2 is a block diagram illustrating a non-limiting exemplary embodiment of an ESPI oxygen imaging system.

Referring to FIG. 2, a block diagram illustrates the modules of a non-limiting exemplary embodiment of the ESPI oxygen imaging system 12 that may execute on one or more processors 20 to produce a high-resolution oxygen image of a sample. The ESPI oxygen imaging system 12 may include modules including, but not limited to, a time point selection module 1000 for selecting the time points within the sets of EPR time history data that may be processed by an ESPI image formation module 1002 that may reconstruct an image of the sample for each time point specified by the time point selection module 1000. An ESPI image comparison module 1004 may compare the pixel or voxel intensity of each ESPI image with the corresponding pixel or voxel intensity of the other images, and determine the rate of decrease of intensity with respect to time for each pixel or voxel in the image. The rates of intensity decrease at each pixel or voxel of the image may be used to determine oxygen concentrations in a oxygen imaging module 1006 by looking up oxygen concentrations in a previously stored table of oxygen concentrations as a function of relaxation time $T_2$. In addition, the oxygen imaging module 1006 may map the oxygen concentrations obtained for each pixel or voxel of the image to the spatial location of the corresponding pixel or voxel to produce one or more high-resolution oxygen images. The ESPI oxygen imaging system 12 may also include an image output module 1008 that may display, store, or transmit the one or more high-resolution oxygen images to the output system 16.

Time Point Selection Module

Figure 3:
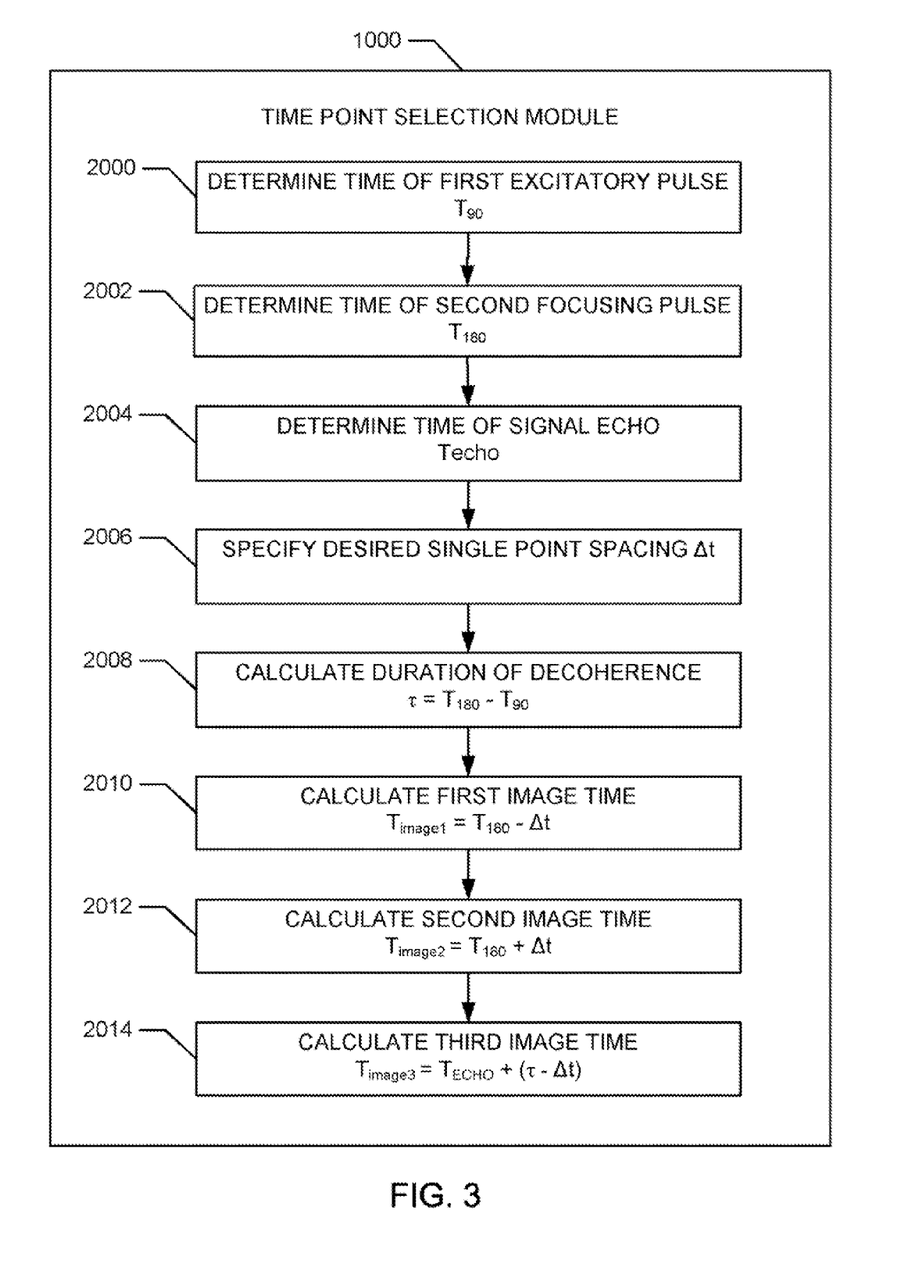
FIG. 3 is a flow chart of the processes of a time point selection module in a non-limiting exemplary embodiment of an ESPI oxygen imaging system.

FIG. 3 is a flow chart of the processes of a time point selection module 1000 in a non-limiting exemplary embodiment of an ESPI oxygen imaging system 12 that identifies two or more time points within the sets of EPR time history data to be reconstructed into high resolution images by the ESPI image formation module 1002. Non-limiting examples of single time points that may be selected for image reconstruction include Δt prior to the second 180° pulse 103, Δt after the second 180° pulse 103, and a time (τ−Δt) after the echo time $T_{echo}$.

Without being bound to any particular theory, single data points that are governed only by $T_2$ relaxation phenomena occur at equal time intervals on either side of the 180° pulse 103 and at equal time intervals on either side of the echo peak 107, enabling the choice of multiple points and proper resizing of the field of view (FOV) to facilitate accurate evaluation of in vivo $pO_2$. In an embodiment, the EPR data may be generated at other specified inter-pulse delays (τ) to generate different $T_2$-weighted echoes. In other embodiments, excitatory pulses other than 90° pulses and focusing pulses other than 180° pulses (θ-t-2θ) may be used to improve measurement times by reducing inter-sequence relaxation delays ($T_R$) and the impact of inter-sequence relaxation delays on oxygen image sensitivity.

Referring again to FIG. 3, $T_{90}$, $T_{180}$, and $T_{echo}$ may be determined at steps 2000, 2002, and 2004 respectively. A desired time point spacing Δt may be specified at step 2006, and the duration of decoherence τ may be calculated at step 2008. First and second image times specified at a time Δt before and after the focusing pulse 103 may be calculated at steps 2010 and 2012 respectively. Optionally, a third image time may be calculated at (τ−Δt) after the echo peak 107.

Referring to FIG. 7, the first image time 111, the second image time 113, and the third image time 115 are identified on the lower graph showing the log of the EPR signal intensity 109 as a function of time.

ESPI Image Formation Module

In an embodiment, images of the sample are constructed using a SPI procedure that processes a pair of specified time points 111 and 113 juxtaposed on either side of the second 180° pulse 103 of a spin probe system. The sets of EPR data measured by the EPR scanner 14 are subjected to pure phase encoding to generate high-resolution images having identical fields of view and weighted relative to one another in intensity by the $T_2$ of the spin system. Because any de-phasing due to intrinsic magnetic susceptibility of the sample as well as the effects of the phase-encoding gradient are refocused by the 180° pulse 103 between the two specified time points 111 and 113, the images from these two points have identical fields of view and therefore may be compared by the ESPI image comparison module 1004 without further adjustment. In this embodiment, the second 180° pulse 103 nullifies any imaging zoom-in effect attributable to differences in delay relative to the 180° pulse 103 between the first time point 111 and the second specified point 113. Therefore, images reconstructed in this embodiment may be relatively $T_2$-weighted. This particular embodiment obtains high-resolution images comparable to those obtained using previous SPI procedures, as well as obtaining $T_2$ contrasting of the image pixels or voxels comparable to the contrast achieved by previous spin echo analysis procedures, making possible reliable functional physiological EPR imaging.

In another embodiment, image reconstruction may be carried out at other specified inter-pulse delays (τ) to generate different $T_2$-weighted echoes. The set of different $T_2$-weighted echoes corresponding to different specified values of τ may be Fourier-transformed and back-projected to provide $T_2$-weighted images.

Figure 4:
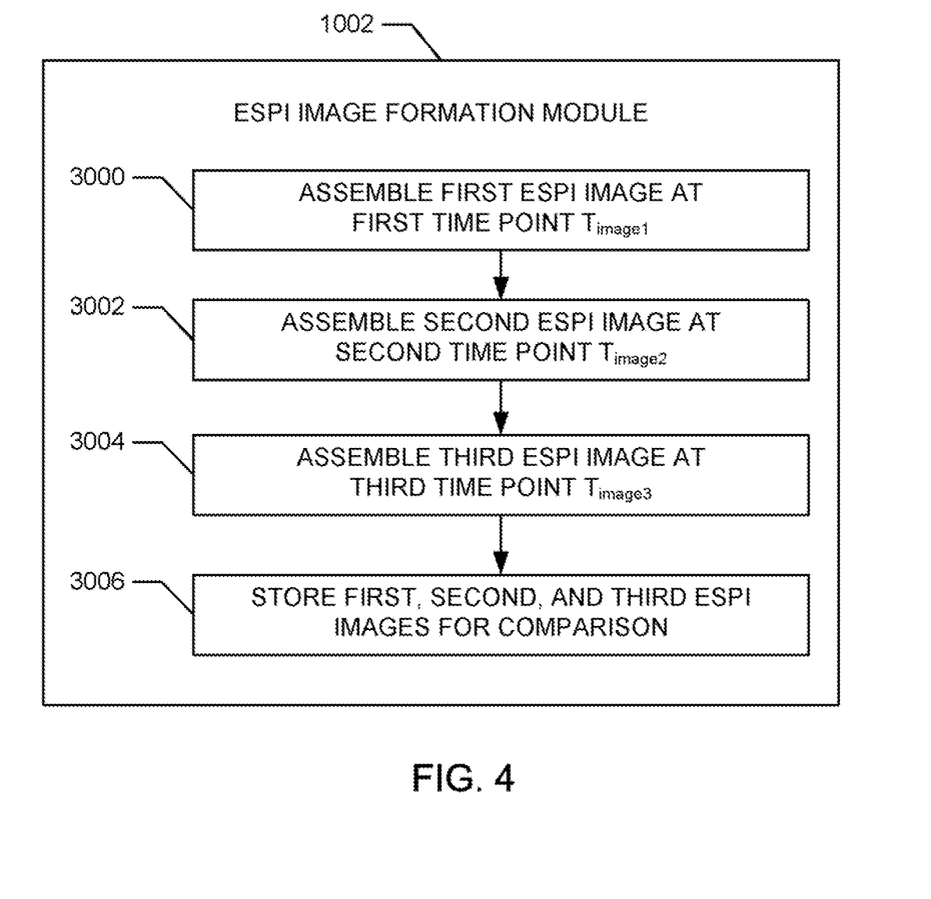
FIG. 4 is a flow chart of the processes of an ESPI image formation module in a non-limiting exemplary embodiment of an ESPI oxygen imaging system.

FIG. 4 is a flow chart of the processes of an ESPI image formation module 1002 in a non-limiting exemplary embodiment of an ESPI oxygen imaging system 12. The ESPI image formation module 1002 may assemble the first, second and third ESPI images corresponding to the three image times $T_{image1}$, $T_{image2}$, $T_{image3}$ calculated by the time point selection module 1000 at steps 3000, 3002, and 3004 respectively. Each of the three images may be stored at step 3006.

ESPI Image Comparison Module

In an embodiment, the ESPI image comparison module 1004 may assess the pixel-wise decay of spin intensities that may be used to derive a spatially-resolved $T_2$. Referring again to FIG. 7, a linear relationship 117 is illustrated between the log of signal intensity 109 at the three image times 111, 113, and 115. In another embodiment, multiple triplets of single time points from a given analytical run corresponding to different values of Δt may be used, after properly resizing the field of view, to obtain a statistically reliable estimate of $T_2$.

Without being bound to any particular theory, the free induction decay (FID) of the intensities of each triplet of single time points is likely to be governed by true $T_2$, as demonstrated by simulation. In addition, field inhomogeneity and susceptibility contributions to the FID of the intensities of each triplet of single time points most likely cancels out. Thus, in an embodiment, a single echo-SPI run may provide from about 1 to about 3 different triplets of single time points corresponding to a total number of single time points including but not limited to 3, 6 or 9 single time points for the evaluation of spatially-resolved $T_2$ after proper resizing of the images.

Figure 5:
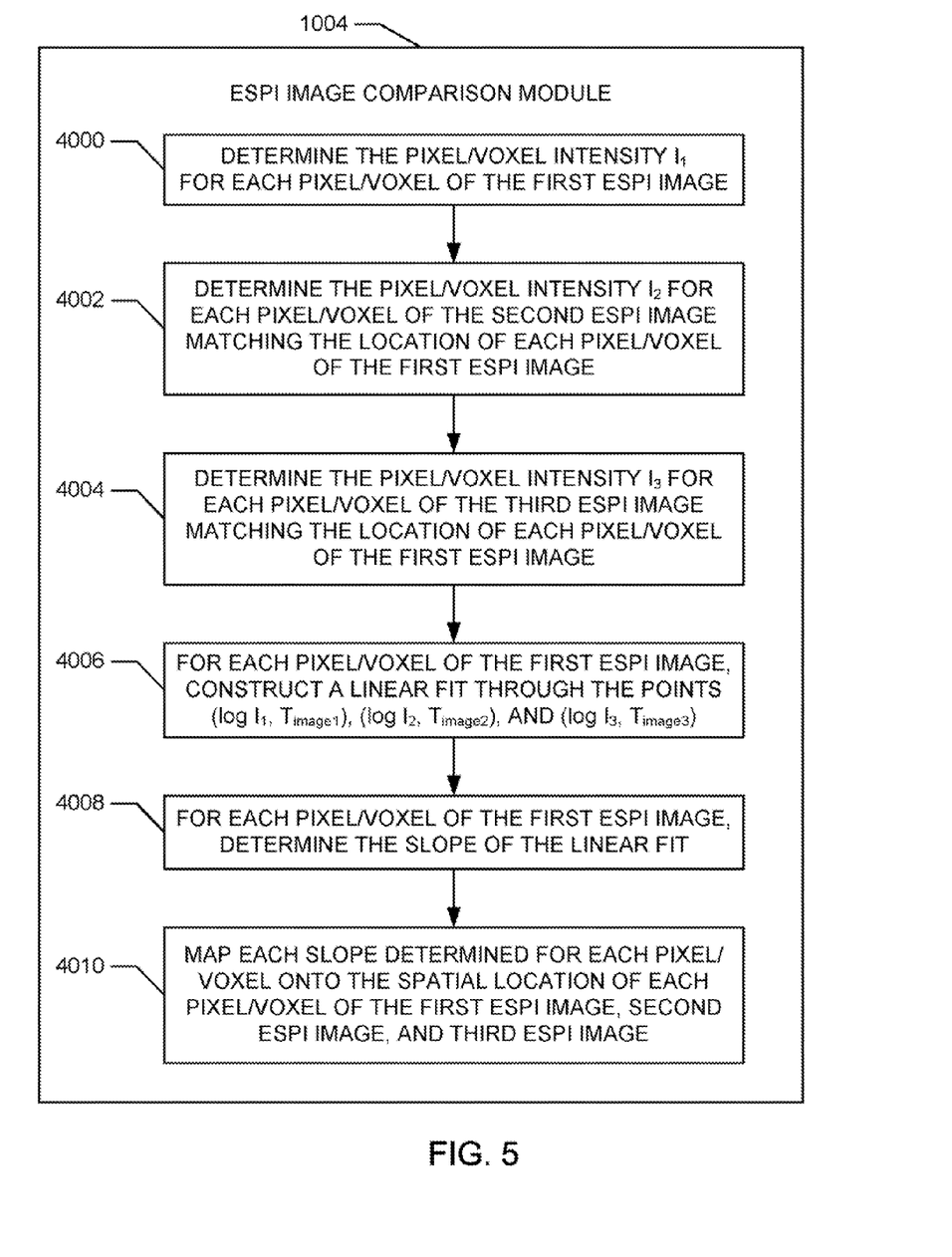
FIG. 5 is a flow chart of the processes of an ESPI image comparison module in a non-limiting exemplary embodiment of an ESPI oxygen imaging system.

FIG. 5 is a flow chart of the processes of an ESPI image comparison module 1004 in a non-limiting exemplary embodiment of an ESPI oxygen imaging system 12. The intensities $I_1$, $I_2$, and $I_3$ for the corresponding pixels or voxels of the first, second, and third images are determined in steps 4000, 4002, and 4004 respectively. For each corresponding pixel or voxel of the images, a linear fit through the triplet of points (log $I_1$, $T_{image1}$), (log $I_2$, $T_{image2}$) and (log $I_3$, $T_{image3}$) may be determined at step 4006. The slope of the curve fits for each pixel/voxel, which is a statistical estimate of $T_2$, may be determined at step 4008 and mapped onto the spatial location of the pixels/voxels in the image at step 4010.

Oxygen Imaging Module

In an embodiment, the spatially-resolved $T_2$ estimated by the ESPI image comparison module 1004 may be compared by the oxygen imaging module 1006 to known relaxivities of dissolved oxygen at various $pO_2$ values and used to perform a quantitative evaluation of in vivo spatial mapping of $pO_2$ within the subject. Using suitably controlled, interleaved, multi-gradient measurements, the image intensities may be calibrated as a function of delay of the time point relative to the excitation pulse, and quantitative oxygenation information may be obtained. In other embodiments, the calibration may be performed separately for each size of resonator. In yet other embodiments, calibration with reference standards may be used to correct for the detrimental effects of intrinsic magnetic susceptibility of the subject, in order to produce superior image resolution and oxygen quantitation using SPI procedures.

Figure 6:
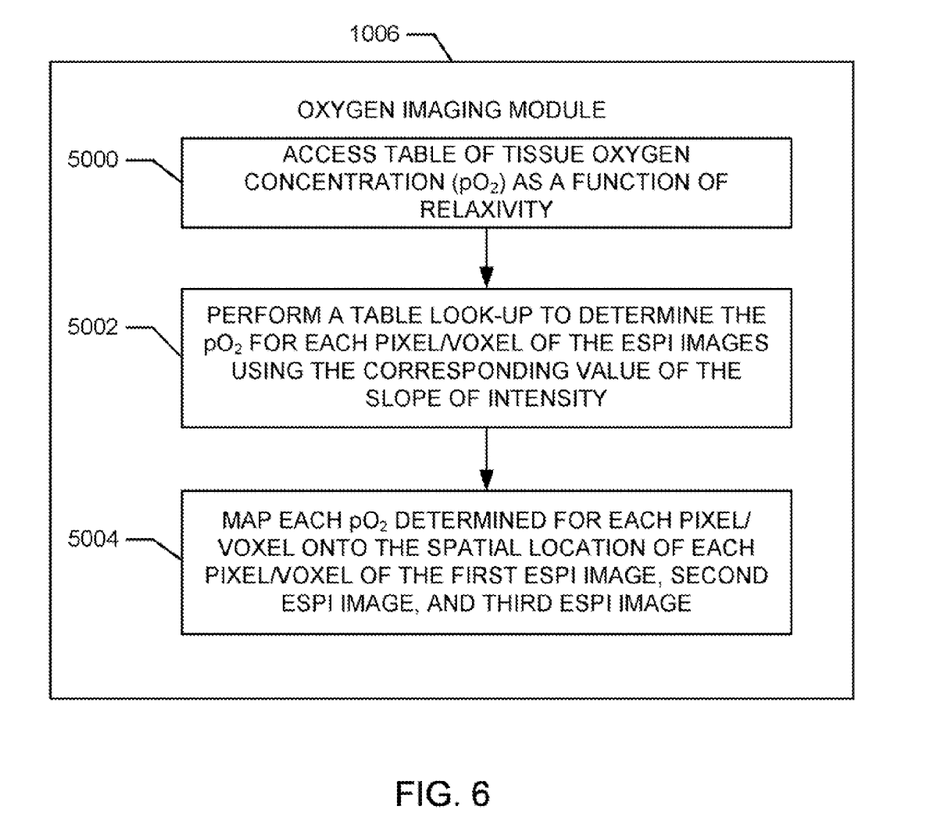
FIG. 6 is a flow chart of the processes of an oxygen imaging module in a non-limiting exemplary embodiment of an ESPI oxygen imaging system.

FIG. 6 is a flow chart of the processes of an oxygen imaging module 1006 in a non-limiting exemplary embodiment of an ESPI oxygen imaging system 12. A table of tissue oxygen concentration ($pO_2$) as a function of relaxivity is accessed at step 5000. The $pO_2$ for each pixel/voxel location of the images are then determined by a table lookup using the slope of pixel intensity decrease from the image map at step 5002, and the $pO_2$ values are mapped onto the spatial locations of the image to produce the high-resolution oxygen image at step 5004.

System Components

Embodiments of the ESPI imaging system 10 may include particular components for providing various functions as discussed above. In particular, the computer readable media 24 may include volatile media, nonvolatile media, removable media, non-removable media, and/or other media or mediums that can be accessed by a general purpose or special purpose computing device. For example, computer readable media 24 may include computer storage media and communication media, including computer readable media. Computer storage media further may include volatile, nonvolatile, removable, and/or non-removable media implemented in a method or technology for storage of information, including but not limited to computer readable instructions, data structures, program modules, and/or other data. Communication media may, for example, embody computer readable instructions, data structures, program modules, algorithms, and/or other data, including as or in a modulated data signal. The communication media may be embodied in a carrier wave or other transport mechanism and may include an information delivery method. The communication media may include wired and/or wireless connections and technologies and may be used to transmit and/or receive wired or wireless communications. Combinations and/or sub-combinations of the systems, components, modules, and methods and processes described herein may be made.

The EPR scanner 14 may include, for example, a hard disk (not shown) that stores the sets of EPR time history data as input files that are read by the ESPI oxygen imaging system 12. The EPR scanner 14 also may include a storage system that stores electronic data, including but not limited to the sets of EPR time history data and other electronic data files. The EPR scanner 14 also may include one or more processing systems and/or communication systems that transmit and/or receive electronic files and/or other electronic document information or data through wireless and/or wire line communication systems, and/or other data to the ESPI oxygen imaging system 12.

The output system 16 may include a communication system that communicates data with another system or component. The output system 16 may be a storage system that temporarily and/or permanently stores data, including but not limited to input files, intermediate data tables generated by the ESPI oxygen imaging system 12, output files, and/or other data. The output system 16 also may include a computer, one or more processors, one or more processing systems, or one or more processes that further process data. The output system 16 may otherwise include a monitor or other display device, one or more processors, a computer, a printer, another data output device, volatile and/or nonvolatile memory, other output devices, computer readable media, a user interface 18 for displaying data, and/or a combination of the foregoing. The output system 16 may receive and/or transmit data through a wireless and/or wire line communication system. The output system 16 may be embodied by or in or operate using one or more processors or processing systems, one or more distributed or integrated systems, and/or computer readable media. The output system 16 may be optional for some embodiments.

Applications of Embodiments of ESPI Oxygen Imaging Method

In an embodiment, ESPI oxygen imaging system 12 may be used to perform in vivo functional physiological imaging on small animals that includes high-quality image resolution and quantitative assessment of in vivo tissue oxygenation. Non-limiting examples of applications of this embodiment include the planning and efficacy assessment of radiation and chemotherapeutic treatment for tumors. Another embodiment may make use of a time-domain Fourier Transform EPR imaging (FT-EPRI) procedure with emphasis on spatial and temporal resolution to produce high-resolution oxymetric imaging. The high temporal resolution of this embodiment may be used to observe rapid physiological processes that may require accurate and rapid time-course readings.

The ESPI oxygen imaging system 12 described herein may provide well-resolved EPR images and accurate $T_2$-weighted oxygen quantization for in vivo applications. Non-limiting examples of in vivo applications of various embodiments include the observation of changes in blood perfusion and oxygenation in tumors in substantially real time and the non-invasive analysis of angiogenesis in and around tumors. In addition, the various embodiments of ESPI oxygen imaging system 12 may provide excellent temporal resolution for additional applications including but not limited to the quantification of pharmacokinetics and metabolic degradation kinetics of bioactive free radicals as well as the measurement of tissue oxygenation during ischemia and reperfusion. Other non-biological applications of various embodiments include but are not limited to the characterization of polymers with respect to amorphous and crystalline fractions, materials science, and solid state measurements. Additional uses and applications of the various embodiments will be become apparent to those of skill in the art upon review of this disclosure.

EXAMPLES

The following examples illustrate various aspects of the embodiments.

Example 1

Oxymetric Measurements of Tumor in Mouse Tumor Model

To assess the feasibility of an ESPI oxygen imaging method, the following experiment was conducted. The echo-based SPI EPR imaging/oxymetric method was used to perform imaging of a mouse tumor model (SCC, squamous cell carcinoma) implanted on one leg of a C3H mouse.

Figure 8:
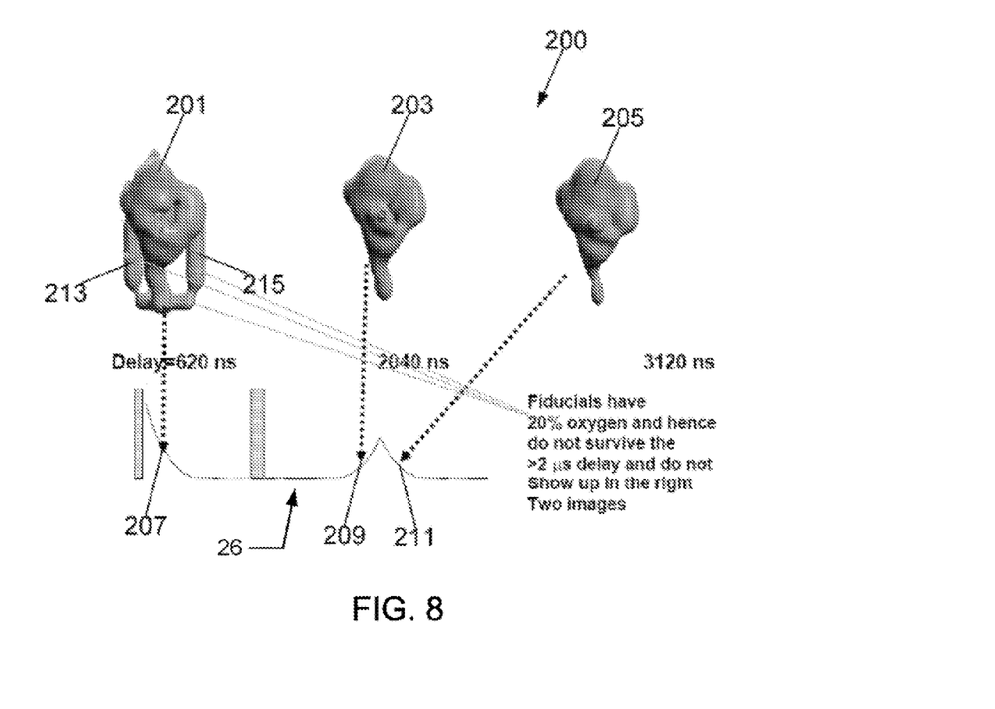
FIG. 8 shows linked timing and spatial plots of a leg with an SCC tumor, including three surface-rendered images taken at times at which the echo-based SPI experiment will produce images of identical size, but weighted by $T_2$.

FIG. 8 is plot combining temporal data and time-dependent image data of the mouse leg with the SCC tumor in the resonator after intravenous injection of the subject with the spin probe Oxo63. The single point images 201, 203, 205 processed at three time points 207, 209, 211 have identical net phase encoding, yielding images of the same size. The echo-based SPI experiment produced images of identical size, but weighted by $T_2$. In particular, the intensity decay which is governed by $T_2$ and not $T_2^*$ allows one to obtain the spatially-resolved $pO_2$.

In the illustrated example, the values $T_{180}-\Delta t$, $T_{180}+\Delta t$, and $T_{echo}+(\tau-\Delta t)$ were set at 620, 2040, 3120 ns respectively for the echo pulse at 1520 ns. The images produced possessed identical size, and were weighted by $T_2$. The additional image components 213 and 215 in the first image 201 at 620 ns were the result of fiducials that contained Oxo63 at 20% $pO_2$; the signals decayed substantially above 2 μs.

Figure 9:
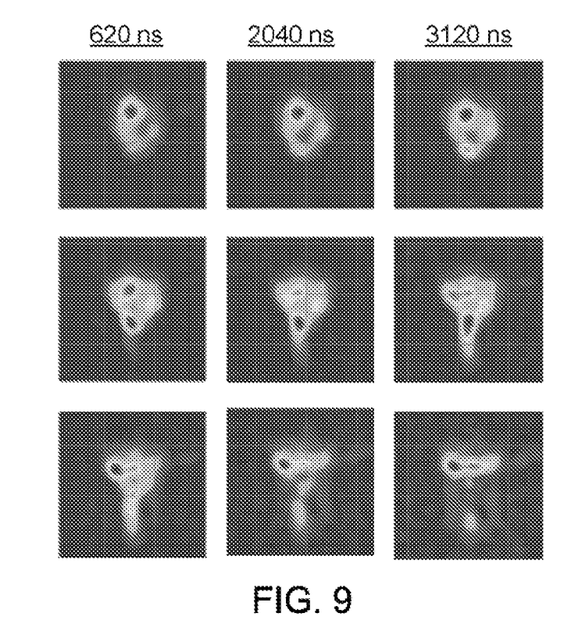
FIG. 9 is a data plot of a collection of slices through orthogonal planes in a three-dimensional spin image.

FIG. 9 illustrates a collection of cross-sectional (sagittal) slices through orthogonal planes in the three-dimensional spin image of the SCC-tumor bearing leg analyzed above are shown produced from single point three-dimensional images of spin distribution generated using a 90°-τ-180° echo sequence. The maximum applied magnetic gradient was 1 G/cm, and the gradient steps were in increments of 1/17 total range in each dimension x, y, z. The echo time (τ) was 1.25 μs. Images with identical Fields Of View (FOV) were processed at 620, 2040, and 3120 ns delay from the first excitation pulse for evaluating $T_2$-based oxymetry.

Figure 10:
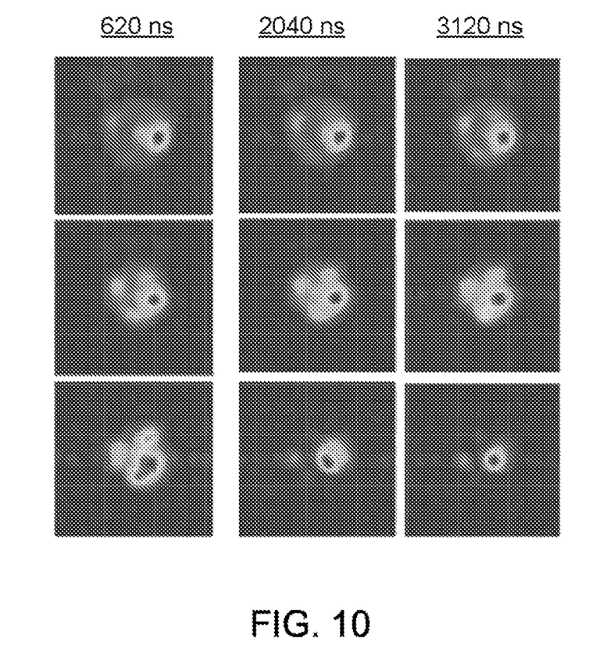
FIG. 10 is a collection of axial slices of a SCC-tumor bearing leg analyzed above from a single point three-dimensional image of spin distribution using a 90°-T-180° echo sequence.

Similarly, FIG. 10 shows a collection of axial slices of the SCC-tumor bearing leg analyzed above from single point three-dimensional image of spin distribution using a 90°-τ-180° echo sequence.

Figure 11:
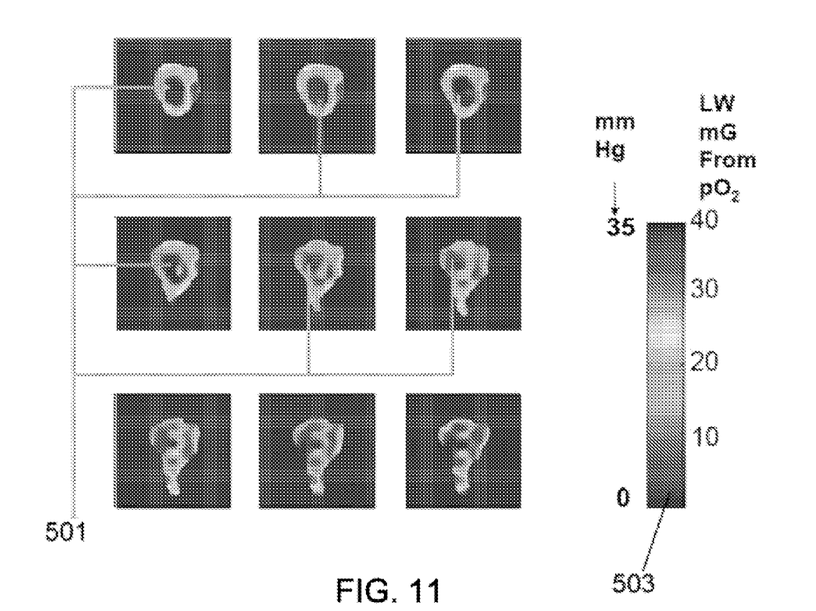
FIG. 11 is a collection of sagittal $pO_2$ slices through a tumor.

FIG. 11 is a collection of sagittal $pO_2$ slices through the tumor 501. The images were derived from a calculation of slopes of intensities in each pixel from three time sequences of images at 620, 2040 and 3120 ns, with the slope of decays being governed by the spin-spin relaxation time $T_2$ in each pixel. From knowledge of the line width ($\propto 1/\Delta T_2$) of the de-aerated spin probe Oxo63, and the value of oxygen relaxivity, since the increase in line width due to $pO_2$ is linear and reproducibly quantitative, one can derive the spatially-resolved $pO_2$ in all regions of the image. The spatially-resolved $pO_2$ were indicated by grayscale, and the grayscale bar 503 in terms of both mGauss of line width and $pO_2$ in terms of mm of Hg. As can be seen, the tip of the leg and the outer tissue surrounding the tumor have a $pO_2$ of about 20-30 mm of Hg. The results obtained agree well with the expected and previously quantified oxygen distribution and heterogeneity in this particular type of tumor.

Figure 12:
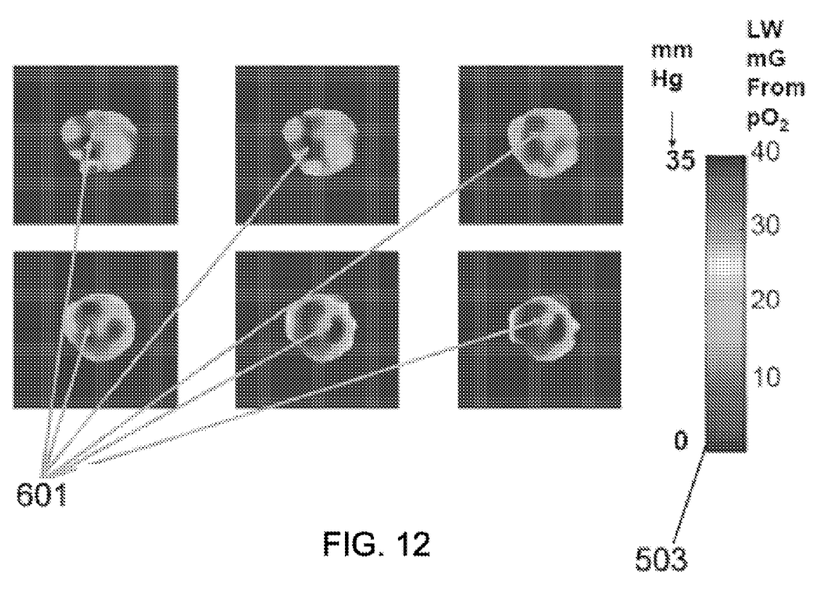
FIG. 12 is a collection of axial $pO_2$ slices through a tumor.

FIG. 12 is a collection of axial $pO_2$ slices through the tumor. The tumor region 601 averages in line width are 0-5 mm of $pO_2$ based on the measured $T_2$ of Oxo63 at 300 MHz.

The results of this experiment indicated that normal leg tissue did not have sufficient spin count to estimate the $pO_2$ accurately at the chosen threshold. The results of this experiment supported the viability of this method and provided high-resolution oxymetric data with true $T_2$-weighting.

Additional objectives, advantages and novel features will be set forth in the description which follows or will become apparent to those skilled in the art upon examination of the drawings and detailed description which follows.

What is claimed is:

1. A method of producing a high-resolution quantitative oxygen image of an in vivo sample comprising: determining at a 90°-τ-180° Hahn echo-based single point imaging (ESPI) oxygen imaging system (12) executing on at least one processor (24) a spatially-resolved relaxivity between each of a plurality of logarithms of spatially-resolved spin intensities of a first ESPI image and each of a plurality of logarithms of spatially-resolved spin intensities of a second ESPI image; and determining at the ESPI oxygen imaging system (12) a spatially-resolved oxygen content by interpolating a reference oxygen concentration from a predetermined table comprising a plurality of reference oxygen concentrations as a function of the spatially-resolved relaxivity, and mapping each spatially-resolved oxygen content onto a corresponding spatial location within a sample image to produce a high-resolution quantitative oxygen image.

2. The method of claim 1, further comprising forming the first ESPI image from a plurality of electron paramagnetic resonance (EPR) signals measured at a time Δt prior to a focusing pulse, and forming the second ESPI image from a plurality of second EPR signals measured at a time Δt after a 180° refocusing pulse.

3. The method of claim 2, further comprising generating the EPR signals by the sample in vivo in response to at least two electromagnetic pulses comprising an excitatory pulse and the refocusing pulse produced by a resonator tuned to a frequency ranging from about 100 MHz to about 2 GHz.

4. The method of claim 1, further comprising perfusing a living tissue with a paramagnetic spin probe, wherein the sample comprises the living tissue.

5. The method of claim 4, wherein the paramagnetic spin probe comprises a biologically compatible molecule.

6. The method according to claim 1, wherein the sample comprises a tumor.

7. A method of producing a high-resolution quantitative oxygen image of an in vivo sample comprising: providing at least two high-resolution 90°-τ-180° Hahn echo-based single point imaging (ESPI) images of the sample comprising: a first ESPI image comprising a reconstruction of a plurality of first EPR signals measured at a time Δt prior to a 180° refocusing pulse, and further comprises a plurality of logarithms of spatially-resolved first spin intensities, wherein each of the first spin intensities is mapped to one of a plurality of spatial positions within a sample image; and, a second ESPI image comprising a reconstruction of a plurality of second EPR signals measured at a time Δt after the refocusing pulse, and further comprises a plurality of logarithms of spatially-resolved second spin intensities, wherein each second spin intensity is mapped to one of the plurality of spatial positions within the sample image; determining for each one of the plurality of spatial positions within the sample image a spatially-resolved relaxivity between each of the plurality of logarithms of spatially-resolved spin intensities of the first ESPI image and each of the plurality of corresponding logarithms of spatially-resolved spin intensities of the second ESPI image; and determining for each one of the plurality of spatial positions within the sample a spatially-resolved oxygen content by interpolating a reference oxygen concentration from a predetermined table comprising a plurality of reference oxygen concentrations as a function of spatially-resolved relaxivities, and mapping each spatially-resolved oxygen content onto a corresponding spatial location within a sample image to produce the high-resolution quantitative oxygen image.

8. The method of claim 7, further comprising generating the EPR signals by the sample in vivo in response to at least two electromagnetic pulses comprising an excitatory pulse and the refocusing pulse produced by a resonator tuned to a frequency ranging from about 100 MHz to about 2 GHz.

9. The method of claim 7, further comprising perfusing a living tissue sample with a paramagnetic spin probe, wherein the sample comprises the living tissue.

10. The method of claim 9, wherein the paramagnetic spin probe comprises a biologically compatible molecule.

11. The method of claim 7, wherein the sample comprises a tumor.

12. A system for producing a high-resolution quantitative oxygen image of an in vivo sample comprising: at least one processor; and, a plurality of modules executed on the at least one processor, the modules comprising: a 90°-τ-180° Hahn echo-based single point imaging (ESPI) image comparison module (1004) to derive a spatially-resolved relaxivity between each of a plurality of logarithms of spatially-resolved spin intensities of a first ESPI image and each of a plurality of logarithms of spatially-resolved spin intensities of a second ESPI image; and an oxygen imaging module (1006) to: determine a spatially-resolved oxygen concentration by interpolating a reference oxygen concentration from a predetermined table comprising a plurality of reference oxygen concentrations as a function of the spatially-resolved relaxivity, and mapping each spatially-resolved oxygen concentration onto a corresponding spatial location within a sample image to produce the high-resolution quantitative oxygen image.

13. The system of claim 12, further comprising: a EPR scanner (14) to generate a set of EPR time history data from a sample and transfer the set of EPR time history data to an ESPI oxygen imaging system (12).

14. The system of claim 13, further comprising: a time point selection module (1000) to identify two or more time points within the sets of EPR time history data to be reconstructed into two or more high-resolution images, wherein the two or more time points comprise a first time of Δt prior to a 180° refocusing pulse and a second time of Δt after the refocusing pulse.

15. The system of claim 12, further comprising: an ESPI image formation module (1002) to construct at least two images of the sample using an echo-based single point imaging procedure, wherein the at least two images comprise a first image constructed using the first time and a second image constructed using the second time.

16. The system of claim 12, further comprising: an image output module (1008) to receive the high-resolution quantitative oxygen image and transmit the high-resolution quantitative oxygen image to an output system for subsequent analysis.

* * * * *